United States Patent
Tomori et al.

(10) Patent No.: US 7,560,549 B2
(45) Date of Patent: Jul. 14, 2009

(54) SULFONYLOXY DERIVATIVES

(75) Inventors: Hiroshi Tomori, Hiratsuka (JP); Hiroshi Miyamoto, Chigasaki (JP); Keijiro Kobayashi, Hiratsuka (JP)

(73) Assignee: Sankyo Company, Limited, Tokyo (JP)

( * ) Notice: Subject to any disclaimer, the term of this patent is extended or adjusted under 35 U.S.C. 154(b) by 517 days.

(21) Appl. No.: 10/590,404

(22) PCT Filed: Feb. 23, 2005

(86) PCT No.: PCT/JP2005/002886

§ 371 (c)(1),
(2), (4) Date: Aug. 23, 2006

(87) PCT Pub. No.: WO2005/080339

PCT Pub. Date: Sep. 1, 2005

(65) Prior Publication Data

US 2007/0135434 A1    Jun. 14, 2007

(30) Foreign Application Priority Data

Feb. 25, 2004  (JP)  ............... 2004-049254

(51) Int. Cl.
*C07D 265/30*  (2006.01)
*C07D 211/06*  (2006.01)

(52) U.S. Cl. ............... 544/158; 544/106; 544/161; 546/184; 546/245

(58) Field of Classification Search ............... 544/106, 544/158, 161; 546/184, 245
See application file for complete search history.

(56) References Cited

U.S. PATENT DOCUMENTS

| | | |
|---|---|---|
| 5,554,763 A | 9/1996 | Emonds-Alt et al. |
| 5,583,134 A | 12/1996 | Emonds-Alt et al. |
| 5,641,777 A | 6/1997 | Emonds-Alt et al. |
| 5,679,693 A | 10/1997 | Emonds-Alt et al. |
| 5,712,288 A | 1/1998 | Emonds-Alt et al. |
| 5,780,466 A | 7/1998 | Emonds-Alt et al. |
| 5,869,663 A | 2/1999 | Emonds-Alt et al. |
| 5,977,359 A | 11/1999 | Emonds-Alt et al. |
| 6,159,967 A | 12/2000 | Nishi et al. |
| 6,392,039 B1 | 5/2002 | Aulombard et al. |
| 6,448,247 B1 | 9/2002 | Nishi et al. |
| 6,511,975 B1 | 1/2003 | Nishi et al. |

FOREIGN PATENT DOCUMENTS

EP    0 591 040 A1    4/1994

OTHER PUBLICATIONS

Kazuhiko Saigo, "Preferred Cystallization," *Survey of Chemistry*, edited by the Chemical Society of Japan, Japan Scientific Societies Press, Tokyo Japan, Kagaku Sousetsu, (1989), No. 6, pp. 32-44.

*Primary Examiner*—Golam M Shameem
(74) *Attorney, Agent, or Firm*—Frishauf, Holtz, Goodman & Chick, P.C.

(57) ABSTRACT

A compound having the formula (I)

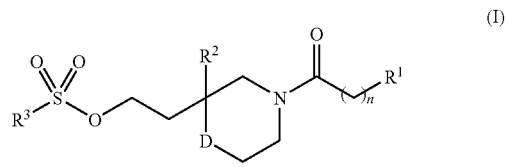

wherein $R^1$ is a substituted phenyl, $R^2$ is a phenyl substituted with halogen atoms, $R^3$ is a substituted phenyl, D is an oxygen or a methylene, and n is 0 or 1. The compound is a synthetic intermediate for a neurokinin receptor antagonist.

27 Claims, No Drawings

SULFONYLOXY DERIVATIVES

This application is a United States national phase application of International Application PCT/JP2005/002886 filed Feb. 23, 2005.

TECHNICAL FIELD

The present invention relates to a sulfonyloxy derivative that is useful as a synthetic intermediate in the preparation of a neurokinin receptor antagonist.

BACKGROUND OF THE INVENTION

A number of effective compounds have been disclosed as neurokinin receptor antagonists (for example, see Patent Literature 1, Patent Literature 2, and Patent Literature 3), and as their synthetic intermediates, for example, compounds having the following structural formulas are disclosed in these patent literatures.

U.S. Pat. No. 5,977,359; Ex. 17 B)

U.S. Pat. No. 5,977,359; Ex. 18 B)

U.S. Pat. No. 6,159,967; Ex. 51 (f)

U.S. Pat. No. 6,159,967; Ex. 70 (e)

In addition, although compounds having the general formula shown below are disclosed in Patent Literature 4, compounds having said general formula wherein $R_I$ represents 2 hydrogen atoms, $R_{II}$ represents a O—$SO_2$—Y group, and Y represents a phenyl or tolyl group have not been specifically disclosed in the said Patent Literature.

m: 2 or 3, Ar: a phenyl group, and the like, A: —O1-$CH_2$—$CH_2$—, and the like, $R_I$: 2 hydrogen atoms, $R_{II}$: O—$SO_2$—Y, Y: a methyl, phenyl tolyl, or $CF_3$ group, or $R_I$: an oxygen atom, $R_{II}$: a hydrogen atom, and T: benzoyl group, and the like It has been generally known that each desired enantiomer in a racemic mixture can be easily separated in high optical purity by preferential crystallization (for example, see Non-patent Literature 1), and this characteristic of racemic mixtures is industrially extremely important. The intermediates described above, however, are not disclosed as racemic mixtures in the literature, and furthermore, there is not any report to suggest that the analogues of these intermediates are racemic mixtures.

[Patent literature 1]
U.S. Pat. No. 5,977,359 Specification
[Patent literature 2]
U.S. Pat. No. 6,159,967 Specification
[Patent literature 3]
U.S. Pat. No. 6,511,975 Specification
[Patent literature 4]
U.S. Pat. No. 5,977,359 Claim 1
[Non-patent literature 1]
Kazuhiko Saigo, Preferential crystallization., Survey of Chemistry No. 6, edited by Chemical Society of Japan, Japan Scientific Societies Press, Tokyo, (1989), p. 32-44.

DISCLOSURE OF THE INVENTION

Subject to be Solved by the Invention

The inventors of the present invention investigated diligently synthetic methods for neurokinin receptor antagonists and, as a result, they discovered that compounds having a sulfonyloxy group in their structure are a racemic mixture, and in addition, each desired enantiomer can be easily separated in high optical purity by conducting preferential crystallization of the racemic mixture. Thus, the present inventors completed the present invention based on the findings described above.

Measures to Solve the Subject

The present invention relates to a compound having the general formula (I) shown below,

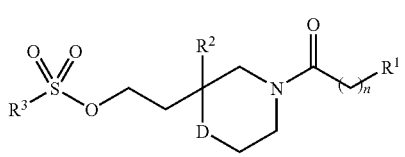

(I)

[wherein,
R¹ represents a phenyl group substituted with from 1 to 3 substituents selected from the group consisting of $C_1$-$C_4$ alkoxy groups and $C_1$-$C_4$ halogenated alkyl groups;
R² represents a phenyl group substituted with from 1 to 3 halogen atoms;
R³ represents a phenyl group substituted with a halogen atom or a nitro group;
D represents an oxygen atom or a methylene group, and
n represents an integer of 0 or 1).
The compound of the above formula (I) is preferably
(2) a compound wherein R¹ is 3-isopropyloxyphenyl, 3,4,5-trimethoxyphenyl or 3,5-bis(trifluoromethyl)phenyl,
(3) a compound wherein R¹ is 3,4,5-trimethoxyphenyl or 3,5-bis(trifluoromethyl)phenyl,
(4) a compound wherein R² is a phenyl group substituted with 1 or 2 fluorine atoms or chlorine atoms,
(5) a compound wherein R² is 3,4-dichlorophenyl,
(6) a compound wherein D is an oxygen atom,
(7) a compound wherein n is 0,
(8) a compound wherein R¹ is 3-isopropyloxyphenyl, D represents a methylene group, and n is 1,
(9) a compound wherein R³ is a phenyl group substituted with a chlorine atom or a nitro group,
(10) any one of the compounds listed below:
 2-[2-(3,4-dichlorophenyl)-4-(3,4,5-trimethoxybenzoyl)morpholin-2-yl]ethyl 4-chlorobenzenesulfonate,
 2-[2-(3,4-dichlorophenyl)-4-(3,4,5-trimethoxybenzoyl)morpholin-2-yl]ethyl 4-nitrobenzenesulfonate,
 2-[2-(3,4-dichlorophenyl)-4-(3,4,5-trimethoxybenzoyl)morpholin-2-yl]ethyl 2-nitrobenzenesulfonate,
 2-[4-[3,5-bis(trifluoromethyl)benzoyl]-2-(3,4-dichlorophenyl)morpholin-2-yl]ethyl 4-chlorobenzenesulfonate,
 2-[4-[3,5-bis(trifluoromethyl)benzoyl]-2-(3,4-dichlorophenyl)morpholin-2-yl]ethyl 4-nitrobenzenesulfonate,
 2-[4-[3,5-bis(trifluoromethyl)benzoyl]-2-(3,4-dichlorophenyl)morpholin-2-yl]ethyl 2-nitrobenzenesulfonate,
 2-[4-{[3,5-bis(trifluoromethyl)phenyl]acetyl}-2-(3,4-dichlorophenyl)morpholin-2-yl]ethyl 4-chlorobenzenesulfonate,
 2-[4-{[3,5-bis(trifluoromethyl)phenyl]acetyl}-2-(3,4-dichlorophenyl)morpholin-2-yl]ethyl 4-nitrobenzenesulfonate,
 2-[4-{[3,5-bis(trifluoromethyl)phenyl]acetyl}-2-(3,4-dichlorophenyl)morpholin-2-yl]ethyl 2-nitrobenzenesulfonate,
 2-[3-(3,4-dichlorophenyl)-1-(3,4,5-trimethoxybenzoyl)piperidin-3-yl]ethyl 4-chlorobenzenesulfonate,
 2-[3-(3,4-dichlorophenyl)-1-(3,4,5-trimethoxybenzoyl)piperidin-3-yl]ethyl 4-nitrobenzenesulfonate,
 2-[3-(3,4-dichlorophenyl)-1-(3,4,5-trimethoxybenzoyl)piperidin-3-yl]ethyl 2-nitrobenzenesulfonate,
 2-[1-[3,5-bis(trifluoromethyl)benzoyl]-3-(3,4-dichlorophenyl)piperidin-3-yl]ethyl 4-chlorobenzenesulfonate,
 2-[1-[3,5-bis(trifluoromethyl)benzoyl]-3-(3,4-dichlorophenyl)piperidin-3-yl]ethyl 4-nitrobenzenesulfonate,
 2-[1-[3,5-bis(trifluoromethyl)benzoyl]-3-(3,4-dichlorophenyl)piperidin-3-yl]ethyl 2-nitrobenzenesulfonate,
 2-[1-{[3,5-bis(trifluoromethyl)phenyl]acetyl}-3-(3,4-dichlorophenyl)piperidin-3-yl]ethyl 4-chlorobenzenesulfonate,
 2-[1-{[3,5-bis(trifluoromethyl)phenyl]acetyl}-3-(3,4-dichlorophenyl)piperidin-3-yl]ethyl 4-nitrobenzenesulfonate, and
 2-[1-{[3,5-bis(trifluoromethyl)phenyl]acetyl}-3-(3,4-dichlorophenyl)piperidin-3-yl]ethyl 2-nitrobenzenesulfonate, and
(11) any one of the compounds listed below:
 2-[2-(3,4-dichlorophenyl)-4-(3,4,5-trimethoxybenzoyl)morpholin-2yl]ethyl 4-chlorobenzenesulfonate,
 2-[4-[3,5-bis(trifluoromethyl)benzoyl]-2-(3,4-dichlorophenyl)morpholin-2-yl]ethyl 4-chlorobenzenesulfonate,
 2-[4-{[3,5-bis(trifluoromethyl)phenyl]acetyl}-2-(3,4-dichlorophenyl)morpholin-2-yl]ethyl 4-chlorobenzenesulfonate,
 2-[3-(3,4-dichlorophenyl)-1-(3,4,5-trimethoxybenzoyl)piperidin-3-yl]ethyl 4-chlorobenzenesulfonate,
 2-[1-[3,5-bis(trifluoromethyl)benzoyl]-3-(3,4-dichlorophenyl)morpholin-2-yl]ethyl 4-chlorobenzenesulfonate, and
 2-[1-{[3,5-bis(trifluoromethyl)phenyl]acetyl}-3-(3,4-dichlorophenyl)morpholin-2-yl]ethyl 4-chlorobenzenesulfonate.
Furthermore, the present invention relates to
(12) a compound, having an enantiomeric excess which is substantially 100%, having the general formula (I') or (I'') shown below,

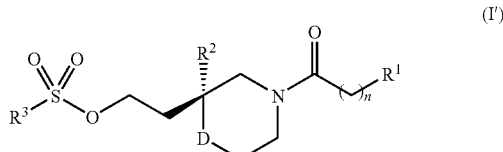

(I')

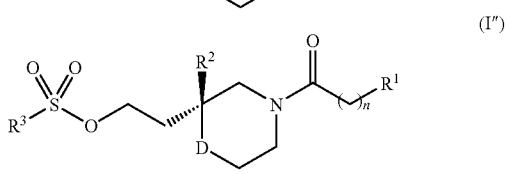

(I'')

(wherein
R¹ represents a phenyl group substituted with from 1 to 3 substituents selected from the group consisting of $C_1$-$C_4$ alkoxy groups and $C_1$-$C_4$ halogenated alkyl groups;

R² represents a phenyl group substituted with from 1 to 3 halogen atoms;
R³ represents a phenyl group substituted with a halogen atom or a nitro group;
D represents an oxygen atom or a methylene group; and
n represents an integer of 0 or 1).

The compound of the above formula (I') or (I") is preferably
(13) a compound wherein R¹ is 3-isopropyloxyphenyl, 3,4,5-trimethoxyphenyl or 3,5-bis(trifluoromethyl)phenyl,
(14) a compound wherein R¹ is 3,4,5-trimethoxyphenyl or 3,5-bis(trifluoromethyl)phenyl,
(15) a compound wherein R² is a phenyl group substituted with 1 or 2 fluorine atoms or chlorine atoms,
(16) a compound wherein R² is 3,4-dichlorophenyl,
(17) a compound wherein D is an oxygen atom,
(18) a compound wherein n is 0,
(19) a compound wherein R¹ is 3-isopropyloxyphenyl, D is a methylene group, and n represents an integer of 1,
(20) a compound wherein R³ is a phenyl group substituted with a chlorine atom or a nitro group,
(21) a compound having the general formula (I'),
(22) any one of the compounds listed below:
  (2R)-2-[2-(3,4-dichlorophenyl)-4-(3,4,5-trimethoxybenzoyl)morpholin-2-yl]ethyl 4-chlorobenzenesulfonate,
  (2R)-2-[2-(3,4-dichlorophenyl)-4-(3,4,5-trimethoxybenzoyl)morpholin-2-yl]ethyl 4-nitrobenzenesulfonate,
  (2R)-2-[2-(3,4-dichlorophenyl)-4-(3,4,5-trimethoxybenzoyl)morpholin-2-yl]ethyl 2-nitrobenzenesulfonate,
  (2R)-2-[4-[3,5-bis(trifluoromethyl)benzoyl]-2-(3,4-dichlorophenyl)morpholin-2-yl]ethyl 4-chlorobenzenesulfonate,
  (2R)-2-[4-[3,5-bis(trifluoromethyl)benzoyl]-2-(3,4-dichlorophenyl)morpholin-2-yl]ethyl 4-nitrobenzenesulfonate,
  (2R)-2-[4-[3,5-bis(trifluoromethyl)benzoyl]-2-(3,4-dichlorophenyl)morpholin-2-yl]ethyl 2-nitrobenzenesulfonate,
  (2R)-2-[4-{[3,5-bis(trifluoromethyl)phenyl]acetyl}-2-(3,4-dichlorophenyl)morpholin-2-yl]ethyl 4-chlorobenzenesulfonate,
  (2R)-2-[4-{[3,5-bis(trifluoromethyl)phenyl]acetyl}-2-(3,4-dichlorophenyl)morpholin-2-yl]ethyl 4-nitrobenzenesulfonate,
  (2R)-2-[4-{[3,5-bis(trifluoromethyl)phenyl]acetyl}-2-(3,4-dichlorophenyl)morpholin-2-yl]ethyl 2-nitrobenzenesulfonate,
  (+)-2-[3-(3,4-dichlorophenyl)-1-(3,4,5-trimethoxybenzoyl)piperidin-3-yl]ethyl 4-chlorobenzenesulfonate,
  (+)-2-[3-(3,4-dichlorophenyl)-1-(3,4,5-trimethoxybenzoyl)piperidin-3-yl]ethyl 4-nitrobenzenesulfonate,
  (+)-2-[3-(3,4-dichlorophenyl)-1-(3,4,5-trimethoxybenzoyl)piperidin-3-yl]ethyl 2-nitrobenzenesulfonate,
  (+)-2-[1-[3,5-bis(trifluoromethyl)benzoyl]-3-(3,4-dichlorophenyl)piperidin-3-yl]ethyl 4-chlorobenzenesulfonate,
  (+)-2-[1-[3,5-bis(trifluoromethyl)benzoyl]-3-(3,4-dichlorophenyl)piperidin-3-yl]ethyl 4-nitrobenzenesulfonate,
  (+)-2-[1-[3,5-bis(trifluoromethyl)benzoyl]-3-(3,4-dichlorophenyl)piperidin-3yl]ethyl 2-nitrobenzenesulfonate,
  (+)-2-[1-{[3,5-bis(trifluoromethyl)phenyl]acetyl}-3-(3,4-dichlorophenyl)piperidin-3-yl]ethyl 4-chlorobenzenesulfonate,
  (+)-2-[1-{[3,5-bis(trifluoromethyl)phenyl]acetyl}-3-(3,4-dichlorophenyl)piperidin-3-yl]ethyl 4-nitrobenzenesulfonate, and
  (+)-2-[1-{[3,5-bis(trifluoromethyl)phenyl]acetyl}-3-(3,4-dichlorophenyl)piperidin-3-yl]ethyl 2-nitrobenzenesulfonate, and
(23) any one of the compounds listed below:
  (2R)-2-[2-(3,4-dichlorophenyl)-4-(3,4,5-trimethoxybenzoyl)morpholin-2-yl]ethyl 4-chlorobenzenesulfonate,
  (2R)-2-[4-[3,5-bis(trifluoromethyl)benzoyl]-2-(3,4-dichlorophenyl)morpholin-2-yl]ethyl 4-chlorobenzenesulfonate,
  (2R)-2-[4-{[3,5-bis(trifluoromethyl)phenyl]acetyl}-2-(3,4-dichlorophenyl)morpholin-2-yl]ethyl 4-chlorobenzenesulfonate,
  (+)-2-[3-(3,4-dichlorophenyl)-1-(3,4,5-trimethoxybenzoyl)piperidin-3-yl]ethyl 4-chlorobenzenesulfonate,
  (+)-2-[3-[3,5-bis(trifluoromethyl)benzoyl]-1-(3,4-dichlorophenyl)piperidin-3-yl]ethyl 4-chlorobenzenesulfonate, and
  (+)-2-[1-{[3,5-bis(trifluoromethyl)phenyl]acetyl}-3-(3,4-dichlorophenyl)piperidin-3-yl]ethyl 4-chlorobenzenesulfonate.

Furthermore, the present invention relates to
(24) a method for obtaining a compound, having an enantiomeric excess which is substantially 100%, having the general formula (I') or (I") by crystallizing a mixture of a compound having the general formula (I') and a compound having the general formula (I")

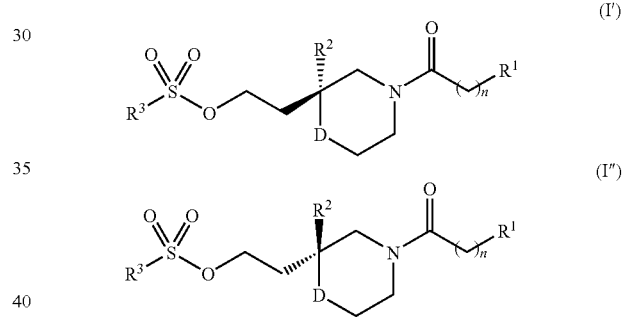

(in the general formulae (I') and (I"),
R¹ represents a phenyl group substituted with 1 to 3 groups selected from the group consisting of $C_1$-$C_4$ alkoxy groups and $C_1$-$C_4$ halogenated alkyl groups;
R² represents a phenyl group substituted with 1 to 3 halogen atoms;
R³ represents a $C_1$-$C_4$ alkyl group, a phenyl group, or a phenyl group substituted with a $C_1$-$C_4$ alkyl group, a halogen atom or a nitro group;
D represents an oxygen atom or a methylene group; and
n represents an integer of 0 or 1).

The method described above is preferably
(25) a method wherein R¹ is 3-isopropyloxyphenyl, 3,4,5-trimethoxyphenyl or 3,5-bis(trifluoromethyl)phenyl,
(26) a method wherein R¹ is 3,4,5-trimethoxyphenyl or 3,5-bis(trifluoromethyl)phenyl,
(27) a method wherein R² is a phenyl group substituted with 1 or 2 fluorine atoms or chlorine atoms,
(28) a method wherein R² is 3,4-dichlorophenyl,
(29) a method wherein R³ is a methyl group, a phenyl group, or a phenyl group substituted with a methyl group, a chlorine atom or a nitro group,
(30) a method wherein D is an oxygen atom,
(31) a method wherein n is 0,

(32) a method wherein R¹ is 3-isopropyloxyphenyl, D is a methylene group, and n is 1,

(33) a method wherein R³ is a phenyl group substituted with a chlorine atom or a nitro group,

(34) a method for obtaining a compound, having an enantiomeric excess which is substantially 100%, having the general formula (I'),

(35) a method for obtaining any one of the compounds listed below:
- (2R)-2-[2-(3,4-dichlorophenyl)-4-(3,4,5-trimethoxybenzoyl)morpholin-2-yl]ethyl 4-chlorobenzenesulfonate,
- (2R)-2-[2-(3,4-dichlorophenyl)-4-(3,4,5-trimethoxybenzoyl)morpholin-2-yl]ethyl 4-nitrobenzenesulfonate,
- (2R)-2-[2-(3,4-dichlorophenyl)-4-(3,4,5-trimethoxybenzoyl)morpholin-2-yl]ethyl 2-nitrobenzenesulfonate,
- (2R)-2-[4-[3,5-bis(trifluoromethyl)benzoyl]-2-(3,4-dichlorophenyl)morpholin-2-yl]ethyl 4-chlorobenzenesulfonate,
- (2R)-2-[4-[3,5-bis(trifluoromethyl)benzoyl]-2-(3,4-dichlorophenyl)morpholin-2-yl]ethyl 4-nitrobenzenesulfonate,
- (2R)-2-[4-[3,5-bis(trifluoromethyl)benzoyl]-2-(3,4-dichlorophenyl)morpholin-2-yl]ethyl 2-nitrobenzenesulfonate,
- (2R)-2-[4-[3,5-bis(trifluoromethyl)benzoyl]-2-(3,4-dichlorophenyl)morpholin-2-yl]ethyl 4-methylbenzenesulfonate
- (2R)-2-[4-[3,5-bis(trifluoromethyl)benzoyl]-2-(3,4-dichlorophenyl)morpholin-2-yl]ethyl benzenesulfonate
- (2R)-2-[4-{[3,5-bis(trifluoromethyl)phenyl]acetyl}-2-(3,4-dichlorophenyl)morpholin-2-yl]ethyl 4-chlorobenzenesulfonate,
- (2R)-2-[4-{[3,5-bis(trifluoromethyl)phenyl]acetyl}-2-(3,4-dichlorophenyl)morpholin-2-yl]ethyl 2-nitrobenzenesulfonate,
- (2R)-2-[4-{[3,5-bis(trifluoromethyl)phenyl]acetyl}-2-(3,4-dichlorophenyl)morpholin-2-yl]ethyl 4-methylbenzenesulfonate,
- (+)-2-[3-(3,4-dichlorophenyl)-1-(3,4,5-trimethoxybenzoyl)piperidin-3-yl]ethyl 4-chlorobenzenesulfonate,
- (+)-2-[3-(3,4-dichlorophenyl)-1-(3,4,5-trimethoxybenzoyl)piperidin-3-yl]ethyl 4-nitrobenzenesulfonate,
- (+)-2-[3-(3,4-dichlorophenyl)-1-(3,4,5-trimethoxybenzoyl)piperidin-3-yl]ethyl 2-nitrobenzenesulfonate,
- (+)-2-[1-[3,5-bis(trifluoromethyl)benzoyl]-3-(3,4-dichlorophenyl)piperidin-3-yl]ethyl 4-chlorobenzenesulfonate,
- (+)-2-[1-[3,5-bis(trifluoromethyl)benzoyl]-3-(3,4-dichlorophenyl)piperidin-3-yl]ethyl 4-nitrobenzenesulfonate,
- (+)-2-[1-[3,5-bis(trifluoromethyl)benzoyl]-3-(3,4-dichlorophenyl)piperidin-3-yl]ethyl 2-nitrobenzenesulfonate,
- (+)-2-[1-[3,5-bis(trifluoromethyl)benzoyl]-3-(3,4-dichlorophenyl)piperidin-3-yl]ethyl 4-methylbenzenesulfonate,
- (+)-2-[1-[3,5-bis(trifluoromethyl)benzoyl]-3-(3,4-dichlorophenyl)piperidin-3-yl]ethyl benzenesulfonate,
- (+)-2-[1-{[3,5-bis(trifluoromethyl)phenyl]acetyl}-3-(3,4-dichlorophenyl)piperidin-3-yl]ethyl 4-chlorobenzenesulfonate,
- (+)-2-[1-{[3,5-bis(trifluoromethyl)phenyl]acetyl}-3-(3,4-dichlorophenyl)piperidin-3-yl]ethyl 2-nitrobenzenesulfonate, and
- (+)-2-[1-{[3,5-bis(trifluoromethyl)phenyl]acetyl}-3-(3,4-dichlorophenyl)piperidin-3-yl]ethyl 4-methylbenzenesulfonate, and

(36) a method for obtaining any one of the compounds listed below:
- (2R)-2-[2-(3,4-dichlorophenyl)-4-(3,4,5-trimethoxybenzoyl)morpholin-2-yl]ethyl 4-chlorobenzenesulfonate,
- (2R)-2-[4-[3,5-bis(trifluoromethyl)benzoyl]-2-(3,4-dichlorophenyl)morpholin-2-yl]ethyl 4-chlorobenzenesulfonate,
- (2R)-2-[4-{[3,5-bis(trifluoromethyl)phenyl]acetyl}-2-(3,4-dichlorophenyl)morpholin-2-yl]ethyl 4-chlorobenzenesulfonate,
- (+)-2-[3-(3,4-dichlorophenyl)-1-(3,4,5-trimethoxybenzoyl)piperidin-3-yl]ethyl 4-chlorobenzenesulfonate,
- (+)-2-[1-[3,5-bis(trifluoromethyl)benzoyl]-3-(3,4-dichlorophenyl)piperidin-3-yl]ethyl 4-chlorobenzenesulfonate, and
- (+)-2-[1-{[3,5-bis(trifluoromethyl)phenyl]acetyl}-3-(3,4-dichlorophenyl)piperidin-3-yl]ethyl 4-chlorobenzenesulfonate.

Furthermore, the present invention relates to

(37) a method for preparing compounds having general formula (III) shown below or pharmaceutically acceptable salts thereof, which is characterized by reacting a compound having general formula (I') shown below with a compound having general formula (II) shown below:

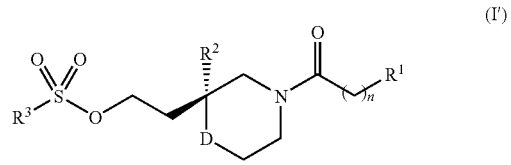

(wherein R¹ represents a phenyl group substituted with 1 to 3 substituents selected from a group consisting of $C_1$-$C_4$ alkoxy groups and $C_1$-$C_4$ halogenated alkyl groups; R² represents a phenyl group substituted with 1 to 3 halogen atoms; R³ represents a phenyl group or a phenyl group substituted with a $C_1$-$C_4$ alkyl group, a halogen atom or a nitro group; D represents an oxygen atom or a methylene group; and n represents an integer of 0 or 1),

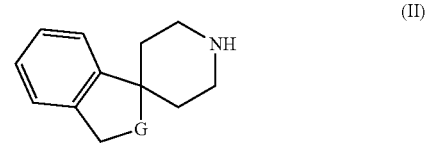

(wherein G represents a >C—OH group or a >S→O group), and

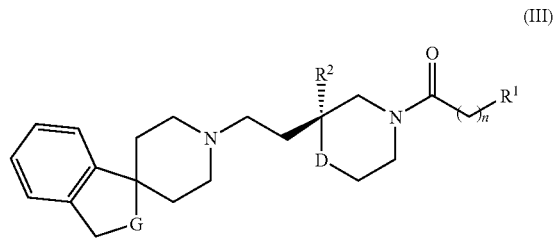

(wherein D, G, R¹, R² and n have the same meanings as those indicated hereinbefore).

Among the above, preferred methods are

(38) a method wherein $R^1$ is 3-isopropyloxyphenyl, 3,4,5-trimethoxyphenyl or 3,5-bis(trifluoromethyl)phenyl,
(39) a method wherein $R^1$ is 3,4,5-trimethoxyphenyl or 3,5-bis(trifluoromethyl)phenyl,
(40) a method wherein $R^2$ is a phenyl group substituted with 1 or 2 fluorine atoms or chlorine atoms,
(41) a method wherein $R^2$ is 3,4-dichlorophenyl,
(42) a method wherein $R^3$ is a phenyl group, or a phenyl group substituted with a methyl group, a chlorine atom or a nitro group,
(43) a method wherein D is an oxygen atom,
(44) a method wherein n is 0,
(45) a method wherein $R^1$ is 3-isopropyloxyphenyl, D is a methylene group, and n is 1,
(46) a method wherein $R^3$ is a phenyl group substituted with a chlorine atom or a nitro group,
(47) a method wherein the compound having general formula (I') is any one of the compounds listed below:
  (2R)-2-[2-(3,4-dichlorophenyl)-4-(3,4,5-trimethoxybenzoyl)morpholin-2-yl]ethyl 4-chlorobenzenesulfonate,
  (2R)-2-[2-(3,4-dichlorophenyl)-4-(3,4,5-trimethoxybenzoyl)morpholin-2-yl]ethyl 4-nitrobenzenesulfonate,
  (2R)-2-[2-(3,4-dichlorophenyl)-4-(3,4,5-trimethoxybenzoyl)morpholin-2-yl]ethyl 2-nitrobenzenesulfonate,
  (2R)-2-[2-(3,4-dichlorophenyl)-4-(3,4,5-trimethoxybenzoyl)morpholin-2-yl]ethyl 4-methylbenzenesulfonate,
  (2R)-2-[2-(3,4-dichlorophenyl)-4-(3,4,5-trimethoxybenzoyl)morpholin-2-yl]ethyl benzenesulfonate,
  (2R)-2-[4-[3,5-bis(trifluoromethyl)benzoyl]-2-(3,4-dichlorophenyl)morpholin-2-yl]ethyl 4-chlorobenzenesulfonate,
  (2R)-2-[4-[3,5-bis(trifluoromethyl)benzoyl]-2-(3,4-dichlorophenyl)morpholin-2-yl]ethyl 4-nitrobenzenesulfonate,
  (2R)-2-[4-[3,5-bis(trifluoromethyl)benzoyl]-2-(3,4-dichlorophenyl)morpholin-2-yl]ethyl 2-nitrobenzenesulfonate,
  (2R)-2-[4-[3,5-bis(trifluoromethyl)benzoyl]-2-(3,4-dichlorophenyl)morpholin-2-yl]ethyl 4-methylbenzenesulfonate,
  (2R)-2-[4-[3,5-bis(trifluoromethyl)benzoyl]-2-(3,4-dichlorophenyl)morpholin-2-yl]ethyl benzenesulfonate,
  (2R)-2-[4-{[3,5-bis(trifluoromethyl)phenyl]acetyl}-2-(3,4-dichlorophenyl)morpholin-2-yl]ethyl 4-chlorobenzenesulfonate,
  (2R)-2-[4-{[3,5-bis(trifluoromethyl)phenyl]acetyl}-2-(3,4-dichlorophenyl)morpholin-2-yl]ethyl 4-nitrobenzenesulfonate,
  (2R)-2-[4-{[3,5-bis(trifluoromethyl)phenyl]acetyl}-2-(3,4-dichlorophenyl)morpholin-2-yl]ethyl 2-nitrobenzenesulfonate,
  (2R)-2-[4-{[3,5-bis(trifluoromethyl)phenyl]acetyl}-2-(3,4-dichlorophenyl)morpholin-2-yl]ethyl 4-methylbenzenesulfonate,
  (2R)-2-[4-{[3,5-bis(trifluoromethyl)phenyl]acetyl}-2-(3,4-dichlorophenyl)morpholin-2-yl]ethyl benzenesulfonate,
  (+)-2-[3-(3,4-dichlorophenyl)-1-(3,4,5-trimethoxybenzoyl)piperidin-3-yl]ethyl 4-chlorobenzenesulfonate,
  (+)-2-[3-(3,4-dichlorophenyl)-1-(3,4,5-trimethoxybenzoyl)piperidin-3-yl]ethyl 4-nitrobenzenesulfonate,
  (+)-2-[3-(3,4-dichlorophenyl)-1-(3,4,5-trimethoxybenzoyl)piperidin-3-yl]ethyl 2-nitrobenzenesulfonate,
  (+)-2-[3-(3,4-dichlorophenyl)-1-(3,4,5-trimethoxybenzoyl)piperidin-3-yl]ethyl 4-methylbenzenesulfonate,
  (+)-2-[3-(3,4-dichlorophenyl)-1-(3,4,5-trimethoxybenzoyl)piperidin-3-yl]ethyl benzenesulfonate,
  (+)-2-[1-[3,5-bis(trifluoromethyl)benzoyl]-3-(3,4-dichlorophenyl)piperidin-3-yl]ethyl 4-chlorobenzenesulfonate,
  (+)-2-[1-[3,5-bis(trifluoromethyl)benzoyl]-3-(3,4-dichlorophenyl)piperidin-3-yl]ethyl 4-nitrobenzenesulfonate,
  (+)-2-[1-[3,5-bis(trifluoromethyl)benzoyl]-3-(3,4-dichlorophenyl)piperidin-3-yl]ethyl 2-nitrobenzenesulfonate,
  (+)-2-[1-[3,5-bis(trifluoromethyl)benzoyl]-3-(3,4-dichlorophenyl)piperidin-3-yl]ethyl 4-methylbenzenesulfonate,
  (+)-2-[1-[3,5-bis(trifluoromethyl)benzoyl]-3-(3,4-dichlorophenyl)piperidin-3-yl]ethyl benzenesulfonate,
  (+)-2-[1-{[3,5-bis(trifluoromethyl)phenyl]acetyl}-3-(3,4-dichlorophenyl)piperidin-3-yl]ethyl 4-chlorobenzenesulfonate,
  (+)-2-[1-{[3,5-bis(trifluoromethyl)phenyl]acetyl}-3-(3,4-dichlorophenyl)piperidin-3-yl]ethyl 4-nitrobenzenesulfonate,
  (+)-2-[1-{[3,5-bis(trifluoromethyl)phenyl]acetyl}-3-(3,4-dichlorophenyl)piperidin-3-yl]ethyl 2-nitrobenzenesulfonate,
  (+)-2-[1-{[3,5-bis(trifluoromethyl)phenyl]acetyl}-3-(3,4-dichlorophenyl)piperidin-3-yl]ethyl 4-methylbenzenesulfonate, and
  (+)-2-[1-{[3,5-bis(trifluoromethyl)phenyl]acetyl}-3-(3,4-dichlorophenyl)piperidin-3-yl]ethyl benzenesulfonate, and
(48) a method wherein the compound having general formula (I') is any one of the compounds listed below:
  (2R)-2-[2-(3,4-dichlorophenyl)-4-(3,4,5-trimethoxybenzoyl)morpholin-2-yl]ethyl 4-chlorobenzenesulfonate,
  (2R)-2-[4-[3,5-bis(trifluoromethyl)benzoyl]-2-(3,4-dichlorophenyl)morpholin-2-yl]ethyl 4-chlorobenzenesulfonate,
  (2R)-2-[4-{[3,5-bis(trifluoromethyl)phenyl]acetyl}-2-(3,4-dichlorophenyl)morpholin-2-yl]ethyl 4-chlorobenzenesulfonate,
  (+)-2-[3-(3,4-dichlorophenyl)-1-(3,4,5-trimethoxybenzoyl)piperidin-3-yl]ethyl 4-chlorobenzenesulfonate,
  (+)-2-[1-[3,5-bis(trifluoromethyl)benzoyl]-3-(3,4-dichlorophenyl)piperidin-3-yl]ethyl 4-chlorobenzenesulfonate, and
  (+)-2-[1-{[3,5-bis(trifluoromethyl)phenyl]acetyl}-3-(3,4-dichlorophenyl)piperidin-3-yl]ethyl 4-chlorobenzenesulfonate.

In the general formulae (I), (I'), (I"), (II), and (III) described above, the $C_1$-$C_4$ alkoxy group of "a phenyl group substituted with 1 to 3 substituents selected from a group consisting of $C_1$-$C_4$ alkoxy groups and $C_1$-$C_4$ halogenated alkyl groups" in the definition of $R^1$ can be, for example, a methoxy, ethoxy, propoxy, isopropoxy, butoxy, isobutoxy, or tert-butoxy group, and is preferably a methoxy, ethoxy, propoxy, or isopropoxy group, and more preferably a methoxy or isopropoxy group.

The $C_1$-$C_4$ halogenated alkyl group of "a phenyl group substituted with 1 to 3 substituents selected from a group consisting of $C_1$-$C_4$ alkoxy groups and $C_1$-$C_4$ halogenated alkyl groups" in the definition of $R^1$ is a group wherein one, two or more than two hydrogen atoms of a $C_1$-$C_4$ alkyl group are substituted with halogen atoms (fluorine atoms, chlorine atoms, bromine atoms, or iodine atoms), and is preferably a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, or 2,2-dibromoethyl group, more preferably a trifluoromethyl, trichloromethyl, difluoromethyl, or fluoromethyl group, and particularly preferably a trifluoromethyl group.

The halogen atom of "a phenyl group substituted with a halogen atom" in the definition of $R^3$ and that of "a phenyl group substituted with 1 to 3 halogen atoms" in the definition of $R^2$ is a fluorine atom, chlorine atom, bromine atom or iodine atom. As to the halogen atom of "a phenyl group substituted with a halogen atom" in the definition of $R^3$, a chlorine atom or a bromine atom is preferable, and a chlorine atom is particularly preferable.

The "$C_1$-$C_4$ alkyl group" and the $C_1$-$C_4$ alkyl of "a phenyl group substituted with a $C_1$-$C_4$ alkyl group" in the definition of $R^3$ can be a straight or branched chain alkyl group such as a methyl, ethyl, propyl, isopropyl, butyl, isobutyl, sec-butyl or tert-butyl group, and is preferably a methyl, ethyl, propyl, isopropyl or butyl group, and particularly preferably a methyl group.

"Enantiomeric excess which is substantially 100%" means that the enantiomeric excess is from 97% to 100%.

Compounds having general formula (I) of the present invention can be prepared, for example, by conducting the reaction according to <Method A> described below.

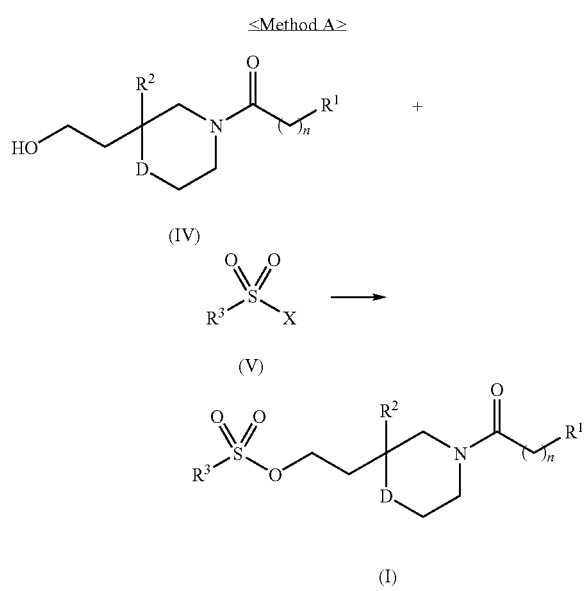

[In the above formulae, D, $R^1$, $R^2$, $R^3$ and n have the same meanings as those indicated hereinbefore, X represents a leaving group (for example, a halogen atom such as a chlorine atom, a bromine atom or an iodine atom, and particularly preferably a chlorine atom)].

The above reaction is conducted in the presence of a base in an inert solvent.

The inert solvent employed in the above reaction is not particularly restricted provided that it has no adverse effect on the reaction and that it dissolves the starting materials at least to some extent, and can be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene, an ester such as ethyl formate, ethyl acetate, propyl acetate, butyl acetate or diethyl carbonate; an ether such as diethyl ether, diisopropyl ether, tert-butyl methyl ether, tetrahydrofuran, dioxane, 1,2-dimethoxyethane or diethyleneglycol dimethyl ether; a ketone such as acetone, ethyl methyl ketone, isobutyl methyl ketone, isophorone or cyclohexanone; a nitro compound such as nitroethane or nitrobenzene; a nitrile such as acetonitrile or isobutyronitrile; an amide such as formamide, N,N-dimethylformamide, N,N-dimethylacetamide, N-methyl-2-pyrrolidone, N-methyl pyrrolidinone or hexamethylphosphoric triamide; a sulfoxide or sulfone such as dimethyl sulfoxide or sulfolane; or a mixture of solvents indicated hereinbefore. The inert solvent is preferably an aromatic hydrocarbon, a halogenated hydrocarbon or a mixture thereof, and particularly preferably toluene, methylene chloride or a mixture thereof.

The base employed in the above reaction is preferably an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-dimethylaminopyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and particularly preferably triethylamine or 4-dimethylaminopyridine.

The reaction temperature employed in the above reaction can be, for example, between −10° C. and 50° C., and preferably between 0° C. and room temperature.

The reaction time varies depending mainly on the reaction temperature, the starting materials, the reaction reagents or the inert solvent to be employed. However, it is usually from 10 minutes to 48 hours, and preferably from 30 minutes to 12 hours.

After completion of the reaction, the desired compound can be isolated from the reaction mixture by conventional treatments.

For example, water is added to the reaction mixture, and the resulting mixture is extracted with an organic solvent immiscible with water such as toluene. The extract is washed with water or the like, dried over anhydrous magnesium sulfate or the like, and evaporated to remove solvent to afford the desired compound.

The compound, the enantiomeric excess of which is substantially 100%, having general formulae (I') or (I") can be obtained by crystallization of the compound having general formula (I) prepared according to the <Method A> described above from a suitable solvent.

The solvent employed in the crystallization is not particularly restricted, and can be, for example, an aliphatic hydrocarbon such as hexane, heptane, methylcyclohexane, ethylcyclohexane, ligroin or petroleum ether; an aromatic hydrocarbon such as benzene, toluene or xylene; an ester such as ethyl formate, methyl acetate, ethyl acetate, propyl acetate, butyl acetate or diethyl carbonate; an alcohol such as methanol, ethanol, propyl alcohol, isopropyl alcohol, butyl alcohol or tert-butyl alcohol; a halogenated hydrocarbon such as methylene chloride, chloroform, carbon tetrachloride, dichloroethane, chlorobenzene or dichlorobenzene; an ether such as diethyl ether, diisopropyl ether, tert-butyl methyl ether, tetrahydrofuran, dioxane, 1,2-dimethoxyethane or diethyleneglycol dimethyl ether; a ketone such as acetone, ethyl methyl ketone, isobutyl methyl ketone, isophorone or cyclohexanone; a nitro compound such as nitroethane or nitrobenzene; a nitrile such as acetonitrile or isobutyronitrile; an amide such as formamide, N,N-dimethylformamide, N,N-dimethylacetamide, N-methyl-2-pyrrolidone, N-methyl-pyrrolidinone or hexamethylphosphoric triamide; a sulfoxide or sulfone such as dimethyl sulfoxide or sulfolane; or a mixture of solvents indicated hereinbefore. The solvent is preferably an aliphatic hydrocarbon, an aromatic hydrocarbon, an ester, an alcohol or a mixture thereof, and particularly preferably hexane, methylcyclohexane, ethylcyclohexane, toluene, ethyl acetate or a mixture thereof.

The temperature employed in the above crystallization varies depending on the solubility of the desired compound in the solvent. However, it is generally between −20° C. and 150° C., preferably between −5° C. and 100° C., and more preferably between 0° C. and 10° C.

The neurokinin receptor antagonist [a compound having general formula (III) or a pharmaceutically acceptable salt thereof] can be prepared using a compound having general formula (I') of the present invention according to <Method B> described below.

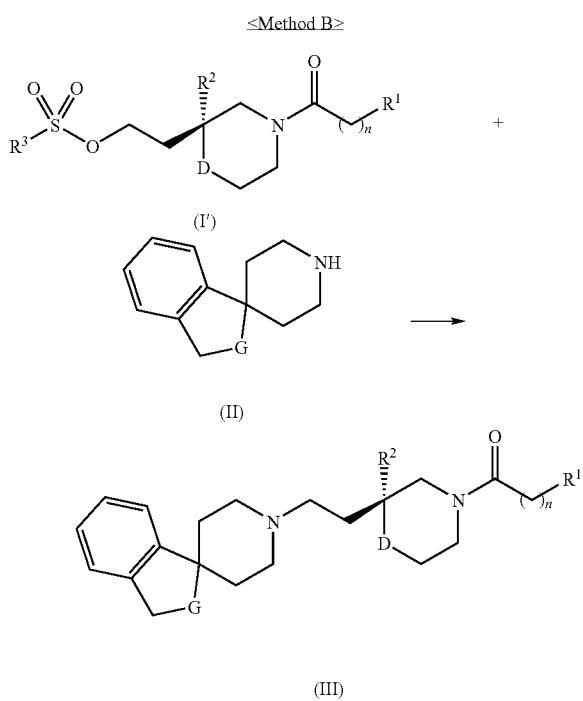

(In the above formulae, D, G, $R^1$, $R^2$, $R^3$ and n have the same meanings as those indicated hereinbefore.)

This step is a step for the preparation of compound (III) by reacting a compound (I') with a compound (II) in the presence of a base in an inert solvent.

The inert solvent to be employed is not particularly restricted provided that it has no adverse effect on the reaction and provided that it dissolves the starting materials at least to some extent, and can be, for example, an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, 1,2-dimethoxyethane or diethyleneglycol dimethyl ether; a ketone such as acetone, ethyl methyl ketone, isobutyl methyl ketone, isophorone or cyclohexanone; a nitro compound such as nitroethane or nitrobenzene; a nitrile such as acetonitrile or isobutyronitrile; an amide such as formamide, N,N-dimethylformamide, N,N-dimethylacetamide, N-methyl-2-pyrrolidone, N-methyl-pyrrolidinone or hexamethylphosphoric triamide; or a sulfoxide or sulfone such as dimethyl sulfoxide or sulfolane. The inert solvent is preferably an amide, an ether or a nitrile, more preferably a nitrile and particularly preferably acetonitrile.

The base to be employed is not particularly restricted provided that it can be used in general reactions as a base, and can be, for example, an alkali metal carbonate such as sodium carbonate, potassium carbonate or lithium carbonate; an alkaline earth metal carbonate such as calcium carbonate or barium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; or an alkaline earth metal hydroxide such as calcium hydroxide or barium hydroxide; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-dimethylaminopyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU). The base is preferably an inorganic base, and most preferably an alkali metal hydrogencarbonate. Furthermore, addition of a catalytic amount of an alkaline metal iodide such as potassium iodide or sodium iodide to the reaction mixture is useful for enhancing the rate of the reaction.

The reaction temperature employed in the above reaction can be, for example, between 0° C. and 150° C., and preferably between 20° C. and 120° C.

The reaction time varies depending mainly on the reaction temperature, the starting materials, the reaction reagent or the inert solvent to be employed. However, it is usually from 30 minutes to 48 hours, and preferably from 1 to 12 hours.

After completion of the reaction, the desired compound can be isolated from the reaction mixture by conventional treatments.

For example, water is added to the reaction mixture, and the resulting mixture is extracted with an organic solvent immiscible with water such as toluene. The extract is washed with water or the like, dried over anhydrous magnesium sulfate or the like, and evaporated to remove solvent to afford the desired compound.

If necessary, the product thus obtained can be separated or purified by conventional treatments, for example, by recrystallization, reprecipitation or by chromatography on a silica gel column.

Furthermore, the pharmaceutically acceptable salt of compound (III), if desired, can be easily prepared by reacting the compound with an acid (the said acid can be, for example, an inorganic acid such as hydrogen chloride, sulfuric acid or phosphoric acid; or an organic acid such as acetic acid, fumaric acid or succinic acid, and is preferably hydrogen chloride or fumaric acid) according to conventional methods.

Compounds to be employed as starting materials in <Method A> and <Method B> described above are disclosed in, for example, U.S. Pat. Nos. 5,977,359, 6,159,967, 6,511,975 and 5,583,134.

Advantage of the Invention

The compound having general formula (I) of the present invention is useful as an intermediate in the preparation of neurokinin receptor antagonists (U.S. Pat. Nos. 5,977,359, 6,159,967, 6,511,975 and 5,583,134). By using the compound having general formula (I), an optically active compound [a compound having general formula (I') or (I") of the present invention] can be obtained with high optical purity by a convenient procedure.

BEST MODE FOR CARRYING OUT THE INVENTION

The present invention will be described in more detail by way of the Examples and Reference Examples below, but the present invention is not limited to these examples.

All the values of enantiomeric excess shown in the examples were determined by high performance liquid chromatography (HPLC). The analysis was carried out under the conditions of "HPLC conditions (1)" described below.

| | <HPLC condition (1)> |
|---|---|
| Column: | CHIRALCEL OD (commercial name, manufactured by Daicel Chemical Industries, Ltd.), 4.6 φ × 250 mm |
| Mobile phase | Hexane:iPrOH = 50:50 |
| Column temperature: | 40° C. |
| Detection | UV (220 nm) |
| Flow rate: | 1 ml/min |

EXAMPLE 1

(2R)-2-[2-(3,4-dichlorophenyl)-4-(3,4,5-trimethoxybenzoyl)morpholin-2-yl]ethyl 4-chlorobenzenesulfonate To a mixture of (2R)-2-[2-(3,4-dichlorophenyl)morpholin-2-yl]ethanol (3.0 g, 10.9 mmol) and methylene chloride (30 ml), triethylamine (4.5 ml, 32.6 mmol) was added under a nitrogen stream, the resulting mixture was cooled to 0-5° C., and then a solution of 3,4,5-trimethoxybenzoyl chloride (2.6 g, 11.1 mmol) in methylene chloride (12 ml) was further added dropwise at below 10° C. After the reaction mixture was stirred at 0-5° C. for 30 minutes, dimethylaminopyridine (0.13 g, 1.1 mmol) was added at the same temperature. Subsequently, to the resulting mixture was added dropwise a solution of 4-chlorobenzenesulfonyl chloride (3.4 g, 16.3 mmol) in methylene chloride (12 ml) at below 10° C., and the resulting mixture was stirred at 0-5° C. for 4 hours. After completion of the reaction, to the reaction mixture was added water (30 ml), and the resulting mixture was partitioned. The separated organic layer was washed successively with 1N hydrochloric acid (30 ml), a 5% aqueous solution of sodium hydrogencarbonate (30 ml) and water (30 ml) and evaporated to dryness. Subsequently, to the residue obtained was added toluene to make the total volume 18 ml, and the resulting mixture was heated at 40° C. Furthermore, to the solution obtained was added methylcyclohexane (9 ml), and the resulting mixture was stirred at 40° C. for 30 minutes, and then at 0-5° C. for 30 minutes. The crystals precipitated were collected by filtration and dried at 50° C. in vacuo to afford the title compound [6.7 g, yield: 95.6%] as a pale yellow crystalline compound.

Thermal analysis (DSC): endothermic peak was observed at 144.0° C.

Powder X-ray diffractometry (diffraction angle 2θ observed when irradiated by Kα ray of copper): 11.62, 14.72, 17.86, 19.46, 20.88, 21.50, 22.84, 24.52°

$^1$H-NMR (400 MHz, CDCl$_3$) δ ppm: 2.00-2.25 (m, 1H), 2.25-2.50 (m, 1H), 3.30-3.90 (m, 6H), 3.86 (s, 9H), 4.00-4.15 (m, 1H), 4.15-4.30 (m, 1H), 6.52 (s, 2H), 6.70-7.90 (m, 7H).

EXAMPLE 2

2-[2-(3,4-Dichlorophenyl)-4-(3,4,5-trimethoxybenzoyl)morpholin-2-yl]ethyl 4-chlorobenzenesulfonate To a mixture of 2-[2-(3,4-dichlorophenyl)morpholin-2-yl]ethanol (4.5 g, 16.1 mmol) and methylene chloride (45 ml), triethylamine (6.7 ml, 48.3 mmol) was added under a nitrogen stream, the resulting mixture was cooled to 0-5° C., and then a solution of 3,4,5-trimethoxybenzoyl chloride (3.8 g, 16.4 mmol) in methylene chloride (18 ml) was further added dropwise at below 10° C. After the mixture was stirred at 0-5° C. for 3 hours, dimethylaminopyridine (0.2 g, 1.6 mmol) was added dropwise at the same temperature. Subsequently, to the resulting mixture was added dropwise a solution of 4-chlorobenzenesulfonyl chloride (5.1 g, 24.2 mmol) in methylene chloride (18 ml) at below 10° C., and the resulting mixture was stirred at 0-5° C. for 3 hours. After completion of the reaction, to the reaction mixture was added water (45 ml), and the resulting mixture was partitioned. The separated organic layer was washed successively with 1N hydrochloric acid (45 ml), a 5% aqueous solution of sodium hydrogencarbonate (45 ml) and water (45 ml) and evaporated to dryness. Subsequently, to the residue obtained was added toluene to make the total volume 27 ml, and the resulting mixture was heated at 40° C. Furthermore, to the solution obtained was added methylcyclohexane (13 ml), and the resulting mixture was stirred at 40° C. for 30 minutes, and then at room temperature for 30 minutes. The crystals precipitated were collected by filtration and dried at 50° C. in vacuo to afford the title compound as a pale yellow crystalline compound.

Thermal analysis (DSC): endothermic peak was observed at 127.5° C.

Powder X-ray diffractometry (diffraction angle 2θ observed when irradiated by Kα ray of copper): 11.46, 14.58, 17.70, 19.30, 20.72, 21.34, 22.70, 24.36°

EXAMPLE 3

(2R)-2-[2-(3,4-dichlorophenyl)-4-(3,4,5-trimethoxybenzoyl)morpholin-2-yl]ethyl 4-nitrobenzenesulfonate To a mixture of (2R)-2-[2-(3,4-dichlorophenyl)morpholin-2-yl]ethanol (25 g, 90.3 mmol) and acetonitrile (125 ml), triethylamine (27.4 g, 271 mmol) was added under a nitrogen stream, the resulting mixture was cooled to 0-5° C., then a solution of 3,4,5-trimethoxybenzoyl chloride (21.24 g, 92.1 mmol) in toluene (100 ml) was further added dropwise at below 10° C., and then the mixture was stirred at 0-5° C. for one hour. After completion of the reaction, toluene (150 ml), water (125 ml) and concentrated hydrochloric acid (25 ml) were added to the reaction mixture, and the resulting mixture was partitioned. The separated organic layer was washed successively with a saturated aqueous solution of sodium hydrogencarbonate and water, and concentrated to afford (2R)-2-[2-(3,4-dichlorophenyl)-4-(3,4,5-trimethoxybenzoyl)morpholin-2-yl]ethanol (44.4 g) as an oil.

Subsequently, to a solution of the oil thus obtained (14.4 g, 30.5 mmol) in methylene chloride (150 ml) were added dimethylaminopyridine (0.37 g, 3.1 mmol) and triethylamine (6.4 ml, 46.0 mmol). After the resulting mixture was cooled to 0-5° C., a solution of 4-nitrobenzenesulfonyl chloride (8.03 g, 36.6 mmol) in methylene chloride (30 ml) was further added dropwise at below 10° C., and then stirred at room temperature for one hour. After completion of the reaction, to the reaction mixture were added water (150 ml) and concentrated hydrochloric acid (7.5 ml), and the resulting mixture was partitioned. The separated organic layer was washed with water twice (150 ml each) and evaporated to dryness. To the residue obtained was added toluene (75 ml), and the resulting mixture was refluxed to dissolve the residue under stirring. The solution thus obtained was cooled to 0-5° C. over about one hour, and stirred at the same temperature for one hour. The crystals precipitated were collected by filtration and dried at 50° C. for 16 hours in vacuo to afford the title compound [18.5 g, yield: 92.3%] as a pale yellow crystalline solid.

Thermal analysis (DSC): endothermic peak was observed at 159.6° C.

Powder X-ray diffractometry (diffraction angle 2θ observed when irradiated by $K_\alpha$ ray of copper): 17.12, 19.02, 20.10, 22.10, 25.20, 27.84°

$^1$H-NMR (400 MHz, CDCl$_3$) δ ppm: 2.07-2.28 (m, 1H), 2.28-2.50 (m, 1H), 3.40-3.85 (m, 6H), 3.86 (s, 6H), 3.87 (s, 3H), 4.10-4.20 (m, 2H), 6.50 (s, 2H), 6.90-7.60 (m, 3H), 7.90-8.10 (m, 2H), 8.35-8.50 (m, 2H).

EXAMPLE 4

2-[2-(3,4-Dichlorophenyl)-4-(3,4,5-trimethoxybenzoyl)morpholin-2-yl]ethyl 4-nitrobenzenesulfonate To a solution of 2-[2-(3,4-dichlorophenyl)morpholin-2-yl]ethanol (5 g, 18.0 mmol) in methylene chloride (25 ml) was added triethylamine (7.5 ml, 54.0 mmol) under a nitrogen stream, the resulting mixture was cooled to 0-5° C., then a solution of 3,4,5-trimethoxybenzoyl chloride (4.2 g, 18.4 mmol) in methylene chloride (20 ml) was further added dropwise at below 10° C. After the resulting mixture was stirred at 0-5° C. for one hour, dimethylaminopyridine (0.22 g, 1.8 mmol) was further added. Subsequently, a solution of 4-nitrobenzenesulfonyl chloride (4.8 g, 21.6 mmol) in methylene chloride (10 ml) was further added dropwise at below 10° C., and the resulting mixture was stirred at room temperature for 30 minutes. After completion of the reaction, to the reaction mixture were added successively water (50 ml) and concentrated hydrochloric acid (5 ml), and the resulting mixture was partitioned. The separated organic layer was washed with water twice (50 ml each) and evaporated to dryness. Subsequently, to the obtained residue was added toluene (45 ml), and the resulting mixture was refluxed to dissolve the residue. The solution thus obtained was cooled to 0-5° C. over about one hour, and stirred at the same temperature for one hour. The crystals precipitated were collected by filtration and dried at 50° C. for 15 hours in vacuo to afford the title compound [11.2 g, yield: 94.9%] as a pale yellow crystalline solid.

Thermal analysis (DSC): endothermic peak was observed at 145.9° C.

Powder X-ray diffractometry (diffraction angle 2θ observed when irradiated by $K_\alpha$ ray of copper): 17.04, 19.00, 20.02, 22.04, 25.18, 27.80°

EXAMPLE 5

(2R)-2-[4-{[3,5-Bis(trifluoromethyl)phenyl]acetyl}-2-(3,4-dichlorophenyl)morpholin-2-yl]ethyl 4-methylbenzenesulfonate To a solution of (2R)-2-[4-{[3,5-bis(trifluoromethyl)phenyl]acetyl}-2-(3,4-dichlorophenyl)morpholin-2-yl]ethanol obtained in Reference Example 1 (3.0 g, 5.7 mmol) in methylene chloride (30 ml) were added dimethylaminopyridine (0.07 g, 0.57 mmol) and triethylamine (1.2 ml, 8.5 mmol) under a nitrogen stream, the resulting mixture was cooled to 0-5° C., and then a solution of 4-methylbenzenesulfonyl chloride (1.3 g, 6.8 mmol) in methylene chloride (10 ml) was further added dropwise at below 10° C. with stirring. After the resulting mixture was stirred at room temperature for 8 hours, to the reaction mixture were added water (30 ml) and concentrated hydrochloric acid (1 ml), and the resulting mixture was partitioned. The separated organic layer was washed with water (30 ml) and evaporated to dryness. The residue obtained was purified by chromatography on a silica gel column and then crystallized from a mixed solvent of toluene (7 ml) and methylcyclohexane (35 ml) under ice-cooling to afford the title compound [2.3 g, yield: 60.3%] as a colorless crystalline solid.

Thermal analysis (DSC): endothermic peak was observed at 105.9° C.

Powder X-ray diffractometry (diffraction angle 2θ observed when irradiated by $K_\alpha$ ray of copper): 16.80, 17.98, 20.08, 20.64, 21.90, 23.64, 25.68°

$^1$H-NMR (400 MHz, CDCL$_3$) δ ppm: 2.07 (ddd, J=14.6, 6.8, 6.8 Hz, 1H), 2.17 (ddd, J=14.6, 6.4, 6.4 Hz, 1H), 2.45 (s, 3H), 3.32 (d, J=14.1 Hz, 1H), 3.40-3.55 (m, 3H), 3.70-3.85 (m, 2H), 3.75 (s, 2H), 4.04 (ddd, J=10.5, 6.4, 6.4 Hz, 1H), 4.51 (d, J=14.1 Hz, 1H), 7.10 (dd, J=8.3, 2.2 Hz, 1H), 7.30 (d, J=8.3 Hz, 1H), 7.30-7.35 (m, 2H), 7.41 (d, J=2.2 Hz, 1H), 7.57 (s, 2H), 7.65-7.73 (m, 2H), 7.76 (s, 1H).

EXAMPLE 6

2-[4-{[3,5-Bis(trifluoromethyl)phenyl]acetyl}-2-(3,4-dichlorophenyl)morpholin-2-yl]ethyl 4-methylbenzenesulfonate To a solution of 2-[4-{[3,5-bis(trifluoromethyl)phenyl]acetyl}-2-(3,4-dichlorophenyl)morpholin-2-yl]ethanol obtained in Reference Example 2 (2.3 g, 4.3 mmol) in methylene chloride (23 ml) were added dimethylaminopyridine (0.05 g, 0.43 mmol) and triethylamine (0.9 ml, 6.5 mmol) under a nitrogen stream, the resulting mixture was cooled to 0-5° C., and then a solution of 4-methylbenzenesulfonyl chloride (1.1 g, 5.6 mmol) in methylene chloride (7 ml) was further added dropwise at below 10° C. After stirring at room temperature for 8 hours, water (23 ml) and concentrated hydrochloric acid (1 ml) were added to the reaction mixture, and the resulting mixture was partitioned. The separated organic layer was washed with water (30 ml) and evaporated to dryness. The residue obtained was purified by chromatography on a silica gel column and then crystallized from a mixed solvent of toluene (3.2 ml) and methylcyclohexane (32 ml) under ice-cooling to afford the title compound [1.9 g, yield: 63.9%] as a colorless crystalline solid.

Thermal analysis (DSC): endothermic peak was observed at 88.4° C.

Powder X-ray diffractometry (diffraction angle 2θ observed when irradiated by $K_\alpha$ ray of copper): 16.70, 17.88, 20.04, 20.56, 21.80, 23.56, 25.64°

EXAMPLE 7

(2R)-2-[4-{[3,5-B s(trifluoromethyl)phenyl]acetyl}-2-(3,4-dichlorophenyl)morpholin-2-yl]ethyl 4-chlorobenzenesulfonate To a solution of (2R)-2-[4-{[3,5-bis(trifluoromethyl)phenyl]acetyl}-2-(3,4-dichlorophenyl)morpholin-2-yl]ethanol obtained in Reference Example 1 (3.0 g, 5.7 mmol) in methylene chloride (30 ml) were added dimethylaminopyridine (0.07 g, 0.57 mmol) and triethylamine (1.2 ml, 8.5 mmol) under a nitrogen stream, the resulting mixture was cooled to 0-5° C., and then a solution of 4-chlorobenzenesulfonyl chloride (1.4 g, 6.8 mmol) in methylene chloride (10 ml) was further added dropwise at below 10° C. After stirring at 0-5° C. for 4 hours, water (30 ml) and concentrated hydrochloric acid (1 ml) were added to the reaction mixture, and the resulting mixture was partitioned. The separated organic layer was washed with water (30 ml) and evaporated to dryness. The residue obtained was purified by chromatography on a silica gel column and then crystallized from a mixed solvent of ethyl acetate (6 ml) and methylcyclohexane (18 ml) under ice-cooling to afford the title compound [2.4 g, yield: 59.6%] as a colorless crystalline solid.

Thermal analysis (DSC): endothermic peak was observed at 136.6° C.

Powder X-ray diffractometry (diffraction angle 2θ observed when irradiated by $K_\alpha$ ray of copper): 16.74, 17.98, 19.96, 20.50, 21.88, 23.68, 25.72°

$^1$H-NMR (400 MHz, CDCl$_3$) δ ppm: 2.10 (ddd, J=14,1. 7.0, 7.0 Hz, 1H), 2.19 (ddd, J=12.4, 6.3, 6.3 Hz, 1H), 3.33 (d, J=13.9 Hz, 1H), 3.42-3.52 (m, 3H), 3.68-3.82 (m, 2H), 3.75 (s, 2H), 4.08 (ddd, J=10.4, 6.3, 6.3 Hz, 1H), 4.56 (d, J=13.9 Hz, 1H), 7.11 (dd, J=8.3, 2.2 Hz, 1H), 7.34 (d, J=8.3 Hz, 1H), 7.42 (d, J=2.2 Hz, 1H), 7.49-7.54 (m, 2H), 7.57 (s, 2H), 7.73-7.78 (m, 3H).

EXAMPLE 8

2-[4-{[3,5-Bis(trifluoromethyl)phenyl]acetyl}-2-(3,4-dichlorophenyl)morpholin-2-yl]ethyl 4-chlorobenzenesulfonate To a solution of 2-[4-{[3,5-bis(trifluoromethyl)phenyl]acetyl}-2-(3,4-dichlorophenyl)morpholin-2-yl]ethanol obtained in Reference Example 2 (2.0 g, 3.8 mmol) in methylene chloride (20 ml) were added dimethylaminopyridine (0.05 g, 0.38 mmol) and triethylamine (0.8 ml, 5.7 mmol) under a nitrogen stream, the resulting mixture was cooled to 0-5° C., and then a solution of 4-chlorobenzenesulfonyl chloride (0.96 g, 4.5 mmol) in methylene chloride (6 ml) was further added dropwise at below 10° C. After stirring at 0-5° C. for 6 hours, water (20 ml) and concentrated hydrochloric acid (0.5 ml) were added to the reaction mixture, and the resulting mixture was partitioned. The separated organic layer was washed with water (20 ml) and evaporated to dryness. The residue obtained was purified by chromatography on a silica gel column and then crystallized from a mixed solvent of ethyl acetate (2.4 ml) and methylcyclohexane (24 ml) under ice-cooling to afford the title compound [1.3 g, yield: 47.6%] as a colorless crystalline solid.

Thermal analysis (DSC): endothermic peak was observed at 11 7.8° C.

Powder X-ray diffractometry (diffraction angle 2θ observed when irradiated by $K_\alpha$ ray of copper): 16.72, 17.94, 19.96, 20.52, 21.86, 23.66, 25.72°

EXAMPLE 9

Purification of (2R)-2-[2-(3,4-dichlorophenyl)-4-(3,4,5-trimethoxybenzoyl)morpholin-2-yl]ethyl 4-chlorobenzenesulfonate with Low Optical Purity To (2R)-2-[2-(3,4-dichlorophenyl)-4-(3,4,5-trimethoxybenzoyl)morpholin-2-yl]ethyl 4-chlorobenzenesulfonate with an enantiomeric excess of 70.5% (5.00 g, 7.8 mmol) was added toluene (11 ml), and the resulting mixture was heated at 80° C. to dissolve the crystalline solid. The solution thus obtained was cooled to 50° C. and stirred at the same temperature for one hour. The solution was cooled to 0-5° C. over about 1.5 hours and further stirred at the same temperature for one hour. The crystals precipitated were collected by filtration and dried at 50° C. in vacuo to afford (2R)-2-[2-(3,4-dichlorophenyl)-4-(3,4,5-trimethoxybenzoyl)morpholin-2-yl]ethyl 4-chlorobenzenesulfonate with an enantiomeric excess of 100% [3.92 g, yield: 78.5%] as a colorless crystalline solid.

EXAMPLE 10

Purification of (2R)-2-[2-(3,4-dichlorophenyl)-4-(3,4,5-trimethoxybenzoyl)morpholin-2-yl]ethyl 4-chlorobenzenesulfonate with Low Optical Purity To (2R)-2-[2-(3,4-dichlorophenyl)-4-(3,4,5-trimethoxybenzoyl)morpholin-2-yl]ethyl 4-chlorobenzenesulfonate with an enantiomeric excess of 80.9% (5.00 g, 7.8 mmol) was added toluene (11 ml), and the resulting mixture was heated at 80° C. to dissolve the crystalline solid. The solution thus obtained was cooled to 50° C. and stirred at the same temperature for one hour. The solution was cooled to 0-5° C. over about 1.5 hours and further stirred at the same temperature for one hour. The crystals precipitated were collected by filtration and dried at 50° C. in vacuo to afford (2R)-2-[2-(3,4-dichlorophenyl)-4-(3,4,5-trimethoxybenzoyl)morpholin-2-yl]ethyl 4-chlorobenzenesulfonate with an enantiomeric excess of 100% [4.18 g, yield: 83.5%] as a colorless crystalline solid.

EXAMPLE 11

Purification of (2R)-2-[2-(3,4-dichlorophenyl)-4-(3,4,5-trimethoxybenzoyl)morpholin-2-yl]ethyl 4-chlorobenzenesulfonate with Low Optical Purity To (2R)-2-[2-(3,4-dichlorophenyl)-4-(3,4,5-trimethoxybenzoyl)morpholin-2-yl]ethyl 4-chlorobenzenesulfonate with an enantiomeric excess of 51.1% (5.00 g, 7.8 mmol) was added toluene (25 ml), and the resulting mixture was heated at 80° C. to dissolve the crystalline solid. The solution thus obtained was cooled to 20-25° C. and stirred at the same temperature for one hour. The solution was cooled to 0-5° C. and further stirred at the same temperature for one hour. The crystals precipitated were collected by filtration and dried at 50° C. in vacuo to afford (2R)-2-[2-(3,4-dichlorophenyl)-4-(3,4,5-trimethoxybenzoyl)morpholin-2-yl]ethyl 4-chlo-

EXAMPLE 12

Optically Active 2-[3-(3,4-dichlorophenyl)-1-(3,4,5-trimethoxybenzoyl)piperidin-3-yl]ethyl 4-chlorobenzenesulfonate To a solution of (+)-2-[3-(3,4-dichlorophenyl)piperidin-3-yl]ethanol (1.70 g, 6.20 mmol) in tetrahydrofuran (85 ml) was added triethylamine (1.30 ml, 9.35 mmol), and the resulting mixture was cooled to 0-5° C. After cooling, a solution of 3,4,5-trimethoxybenzoyl chloride (1.46 g, 6.33 mmol) in tetrahydrofuran (7 ml) was further added dropwise at below 5° C., and the resulting mixture was stirred at 0-5° C. for 5 hours and then evaporated to dryness in vacuo. Subsequently, to the residue obtained were added methylene chloride (50 ml), triethylamine (1.30 ml, 9.35 mmol) and 4-dimethylaminopyridine (0.076 g, 0.62 mmol), and the resulting mixture was cooled to 0-5° C. After cooling, a solution of 4-chlorobenzenesulfonyl chloride (1.57 g, 7.44 mmol) in methylene chloride (3.5 ml) was further added dropwise at below 5° C., and the resulting mixture was stirred at 0-5° C. for 5 hours. After completion of the reaction, water (50 ml) and concentrated hydrochloric acid (2 ml) were added to the reaction mixture, and the resulting mixture was partitioned. The separated organic layer was washed with water (50 ml) and evaporated in vacuo. The residue obtained was purified by chromatography on a silica gel column and then crystallized from a mixed solvent of ethyl acetate (6.6 ml) and hexane (17.7 ml) under ice-cooling to afford the title compound [3.0 g, yield: 76.3%] as a colorless crystalline solid.

Thermal analysis (DSC): endothermic peak was observed at 106.3° C.

Powder X-ray diffractometry (diffraction angle 2θ observed when irradiated by $K_\alpha$ ray of copper): 11.52, 14.70, 17.40, 18.00, 18.18, 19.42, 20.74, 21.10, 21.48, 24.54, 27.10°

$^1$H-NMR (400 MHz, CDCl$_3$) δ ppm: 1.37-1.55 (m, 1H), 1.55-1.73 (m, 1H), 1.80-1.97 (m, 1H), 2.00-2.20 (m, 3H), 3.25-3.48 (m, 2H), 3.48-3.65 (m, 1H), 3,74-3.90 (m, 2H), 3.83 (s, 6H), 3.85 (s, 3H), 4.10-4.30 (m, 1H), 6.38-6.52 (m, 2H), 7.05-7.23 (m, 1H), 7.28-7.44 (m, 2H), 7.45-7.56 (m, 2H), 7.65-7.82 (m, 2H).

EXAMPLE 13

2-[3-(3,4-Dichlorophenyl)-1-(3,4,5-trimethoxybenzoyl)piperidin-3-yl]ethyl 4-chlorobenzenesulfonate To a solution of 2-[3-(3,4-dichlorophenyl)piperidin-3-yl]ethanol (1.92 g, 7.00 mmol) in tetrahydrofuran (100 ml) was added triethylamine (1.50 ml, 10.8 mmol), and the resulting mixture was cooled to 0-5° C. After cooling, a solution of 3,4,5-trimethoxybenzoyl chloride (1.65 g, 7.14 mmol) in tetrahydrofuran (8 ml) was further added dropwise at below 5° C., and the resulting mixture was stirred at 0-5° C. for 4 hours and then evaporated to dryness in vacuo. To the obtained residue, methylene chloride (50 ml), triethylamine (1.50 ml, 10.8 mmol) and 4-dimethylaminopyridine (0.086 g, 0.70 mmol) were added, and the resulting mixture was cooled to 0-5° C. After cooling, a solution of 4-chlorobenzenesulfonyl chloride (1.77 g, 8.39 mmol) in methylene chloride (4 ml) was further added dropwise at below 5° C., and the resulting mixture was stirred at 0-5° C. for 6 hours. After completion of the reaction, water (50 ml) and concentrated hydrochloric acid (2 ml) were added to the reaction mixture, and the resulting mixture was partitioned. The separated organic layer was washed with water (50 ml) and evaporated in vacuo. The residue obtained was purified by chromatography on a silica gel column and then crystallized from a mixed solvent of ethyl acetate (7.5 ml) and hexane (20.3 ml) under ice-cooling to afford the title compound [3.1 g, yield: 68.9%] as a colorless crystalline solid.

Thermal analysis (DSC): endothermic peak was observed at 96.6° C.

Powder X-ray diffractometry (diffraction angle 2θ observed when irradiated by $K_\alpha$ ray of copper): 11.50, 14.68, 17.38, 18.00, 18.16, 19.40, 20.72, 21.08, 21.48, 24.54, 27.06°

REFERENCE EXAMPLES

Reference Example 1

(2R)-2-[4-{[3,5-Bis(trifluoromethyl)phenyl]acetyl}-2-(3,4-dichlorophenyl)morpholin-2-yl]ethanol To a solution of 3,5-bis(trifluoromethyl)phenylacetic acid (10.0 g, 36.8 mmol) in acetonitrile (100 ml), N,N'-carbonyldiimidazole (9.5 g, 58.8 mmol) was added at room temperature, then (2R)-2-[2-(3,4-dichlorophenyl)morpholin-2-yl]ethanol (17.3 g, 62.5 mol) was further added, and the resulting mixture was stirred at room temperature for 30 minutes. After completion of the reaction, the reaction mixture was evaporated to dryness. To the obtained residue, methylene chloride (100 ml), water (100 ml) and concentrated hydrochloric acid (15 ml) were added, and the resulting mixture was partitioned. The separated organic layer was washed with water twice (100 ml each) and evaporated to dryness. The residue obtained was purified by chromatography on a silica gel column to afford the title compound [13.3 g, yield: 68.1%] as an oil.

$^1$H-NMR (400 MHz, CDCl$_3$) δ ppm: 1.85-2.10 (m, 3H), 3.32 (d, J=14.1Hz, 1H), 3.40-3.70 (m, 5H), 3.75 (s, 2H), 3.83-3.95 (m, 1H), 4.80 (d, J=14.1 Hz, 1H), 7.20-7.30 (m, 1H), 7.35-7.45 (m, 1H), 7.50-7.60 (m, 3H), 7.76 (s, 1H).

Reference Example 2

2-[4-{[3,5-Bis(trifluoromethyl)phenyl]acetyl}-2-(3,4-dichlorophenyl)morpholin-2-yl]ethanol To a solution of 3,5-bis(trifluoromethyl)phenylacetic acid (2.0 g, 7.4 mmol) in acetonitrile (20 ml), N,N'-carbonyldiimidazole (1.3 g, 8.1 mmol) was added at room temperature, then 2-[2-(3,4-dichlorophenyl)morpholin-2-yl]ethanol (2.4 g, 8.8 mmol) was further added, and the resulting mixture was stirred at room temperature for one hour. After completion of the reaction, the reaction mixture was evaporated to dryness. To the obtained residue, methylene chloride (20 ml), water (20 ml) and concentrated hydrochloric acid (2 ml) were added, and the resulting mixture was partitioned. The separated organic layer was washed successively with a 5% aqueous solution of sodium hydroxide (25 ml) and water (20 ml) and evaporated to dryness to afford the title compound [2.3 g, yield: 58.6%] as an oil.

INDUSTRIAL APPLICABILITY

Sulfonyloxy derivatives of the present invention are a racemic mixture, and since the desired optically active enantiomer with high purity can be easily obtained, the compounds of the present invention are useful as synthetic intermediates for the production of neurokinin receptor antagonists.

The invention claimed is:

1. A compound having the formula (I) shown below,

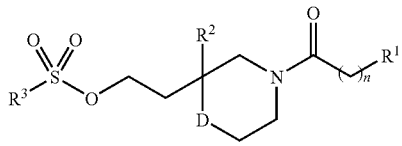

wherein,
R¹ represents a phenyl group substituted with from 1 to 3 substituents selected from the group consisting of $C_1$-$C_4$ alkoxy groups and $C_1$-$C_4$ halogenated alkyl groups;
R² represents a phenyl group substituted with from 1 to 3 halogen atoms;
R³ represents a phenyl group substituted with a halogen atom or a nitro group;
D represents an oxygen atom or a methylene group, and
n represents an integer of 0 or 1.

2. A compound according to claim 1, wherein R¹ is 3-isopropyloxyphenyl, 3,4,5-trimethoxyphenyl or 3,5-bis(trifluoromethyl)phenyl.

3. A compound according to claim 1, wherein R¹ is 3,4,5-trimethoxyphenyl or 3,5-bis(trifluoromethyl)phenyl.

4. A compound according to claim 1, wherein R² is a phenyl group substituted with 1 or 2 fluorine atoms or chlorine atoms.

5. A compound according to claim 1, wherein R² is 3,4-dichlorophenyl.

6. A compound according to claim 1, wherein D is an oxygen atom.

7. A compound according to claim 1, wherein n is 0.

8. A compound according to claim 1, wherein R¹ is 3-isopropyloxyphenyl, D is a methylene group, and n is 1.

9. A compound according to claim 1, wherein R³ is a phenyl group substituted with a chlorine atom or a nitro group.

10. A compound according to claim 1, wherein said compound is selected from the group consisting of
2-[2-(3,4-dichiorophenyl)-4-(3,4,5-trimethoxybenzoyl)morpholin-2-yl]ethyl 4-chlorobenzenesulfonate,
2-[2-(3,4-dichiorophenyl)-4-(3,4,5-trimethoxybenzoyl)morpholin-2-yl]ethyl 4-nitrobenzenesulfonate,
2-[2-(3,4-dichiorophenyl)-4-(3,4,5-trimethoxybenzoyl)morpholin-2-yl]ethyl 2-nitrobenzenesulfonate,
2-[4-[3,5-bis(trifluoromethyl)benzoyl]-2-(3,4-dichlorophenyl)morpholin-2-yl]ethyl 4-chlorobenzenesulfonate,
2-[4-[3,5-bis(trifluoromethyl)benzoyl]-2-(3,4-dichlorophenyl)morpholin-2-yl]ethyl 4-nitrobenzenesulfonate,
2-[4-[3,5-bis(trifluoromethyl)benzoyl]-2-(3,4-dichlorophenyl)morpholin-2-yl]ethyl 2-nitrobenzenesulfonate,
2-[4-{[3,5-bis(trifluoromethyl)phenyl]acetyl}-2-(3,4-dichlorophenyl)morpholin-2-yl]ethyl 4-chlorobenzenesulfonate,
2-[4-{[3,5-bis(trifluoromethyl)phenyl]acetyl}-2-(3,4-dichlorophenyl)morpholin-2-yl]ethyl 4-nitrobenzenesulfonate,
2-[4-{[3,5-bis(trifluoromethyl)phenyl]acetyl}-2-(3,4-dichlorophenyl)morpholin-2-yl]ethyl 2-nitrobenzenesulfonate,
2-[3-(3,4-dichlorophenyl)-1-(3,4,5-trimethoxybenzoyl)piperidin-3-yl]ethyl 4-chlorobenzenesulfonate,
2-[3-(3,4-dichiorophenyl)-1-(3,4,5-trimethoxybenzoyl)piperidin-3-yl]ethyl 4-nitrobenzenesulfonate,
2-[3-(3,4-dichiorophenyl)-1-(3,4,5-trimethoxybenzoyl)piperidin-3-yl]ethyl 2-nitrobenzenesulfonate,
2-[1-[3,5-bis(trifluoromethyl)benzoyl]-3-(3,4-dichlorophenyl)piperidin-3-yl]ethyl 4-chlorobenzenesulfonate,
2-[1-[3,5-bis(trifluoromethyl)benzoyl]-3-(3,4-dichlorophenyl)piperidin-3-yl]ethyl 4-nitrobenzenesultonate,
2-[1-[3,5-bis(trifluoromethyl)benzoyl]-3-(3,4-dichlorophenyl)piperidin-3-yl]ethyl 2-nitrobenzenesulfonate,
2-[1-{[3,5-bis(trifluoromethyl)phenyl]acetyl}-3-(3,4-dichlorophenyl)piperidin-3-yl]ethyl 4-chlorobenzenesulfonate,
2-[1-{[3,5-bis(trifluorornethyl)phenyl]acetyl}-3-(3,4-dichlorophenyl)piperidin-3-yl]ethyl 4-nitrobenzenesulfonate, and
2-[1-{[3,5-bis(trifluoromethyl)phenyl]acetyl}-3-(3,4-dichlorophenyl)piperidin-3-yl]ethyl 2-nitrobenzenesulfonate.

11. A compound according to claim 1, wherein said compound is selected from the group consisting of
2-[2-(3,4-dichlorophenyl)-4-(3,4,5-trimethoxybenzoyl)morpholin-2-yl]ethyl 4-chlorobenzenesulfonate,
2-[4-[3,5-bis(trifluoromethyl)benzoyl]-2-(3,4-dichlorophenyl)morpholin-2-yl]ethyl 4-chlorobenzenesulfonate,
2-[4-{[3,5-bis(trifluoromethyl)phenyl]acetyl}-2-(3,4-dichlorophenyl)morpholin-2-yl]ethyl 4-chlorobenzenesulfonate,
2-[3-(3,4-dichiorophenyl)-1-(3,4,5-trirnethoxybenzoyl)piperidin-3-yl]ethyl 4-chlorobenzenesulfonate,
2-[1-[3,5-bis(trifluoromethyl)benzoyl]-3-(3,4-dichlorophenyl)morpholin-2-yl]ethyl 4-chlorobenzenesulfonate, and
2-[1-{[3,5-bis(trifluoromethyl)phenyl]acetyl}-3-(3,4-dichlorophenyl)morpholin-2-yl]ethyl 4-chlorobenzenesulfonate.

12. A compound, having an enantiomeric excess which is substantially 100%, having the formula (I') or (I'') shown below,

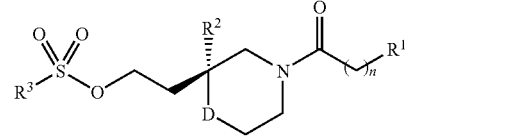

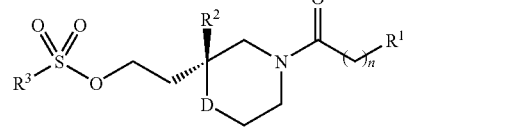

wherein
R¹ represents a phenyl group substituted with from 1 to 3 substituents selected from the group consisting of $C_1$-$C_4$ alkoxy groups and $C_1$-$C_4$ halogenated alkyl groups;
R² represents a phenyl group substituted with from 1 to 3 halogen atoms;
R³ represents a phenyl group substituted with a halogen atom or a nitro group;

D represents an oxygen atom or a methylene group, and n represents an integer of 0 or 1.

13. A compound according to claim 12, wherein $R^1$ is 3-isopropyloxyphenyl, 3,4 5-trimethoxyphenyl or 3,5-bis(trifluoromethyl)phenyl.

14. A compound according to claim 12, wherein $R^1$ is 3,4,5-trimethoxyphenyl or 3,5-bis(trifluoromethyl)phenyl.

15. A compound according to claim 12, wherein $R^2$ is a phenyl group substituted with 1 or 2 fluorine atoms or chlorine atoms.

16. A compound according to claim 12, wherein $R^2$ is 3,4-dichlorophenyl.

17. A compound according to claim 12, wherein D is an oxygen atom.

18. A compound according to claim 12, wherein n is 0.

19. A compound according to claim 12, wherein $R^1$ is 3-isopropyloxyphenyl, D is a methylene group, and n is 1.

20. A compound according to claim 12, wherein $R^3$ is a phenyl group substituted with a chlorine atom or a nitro group.

21. A compound according to claim 12, having the formula (I').

22. A compound according to claim 12, wherein said compound is selected from the group consisting of
 (2R)-2-[2-(3,4-dichlorophenyl)-4-(3,4,5-trimethoxybenzoyl)morpholin-2-yl]ethyl 4-chlorobenzenesulfonate,
 (2R)-2-[2-(3,4-dichlorophenyl)-4-(3,4,5-trimethoxybenzoyl)morpholin-2-yl]ethyl 4-nitrobenzenesulfonate,
 (2R)-2-[2-(3,4-dichlorophenyl)-4-(3,4,5-trimethoxybenzoyl)morpholin-2-yl]ethyl 2-nitrobenzenesulfonate,
 (2R)-2-[4-[3,5-bis(trifluoromethyl)benzoyl]-2-(3,4-dichlorophenyl)morpholin-2-yl]ethyl 4-chlorobenzenesulfonate,
 (2R)-2-[4-[3,5-bis(trifluoromethyl)benzoyl]-2-(3,4-dichlorophenyl)morpholin-2-yl]ethyl 4-nitrobenzenesulfonate,
 (2R)-2-[4-[3,5-bis(trifluoromethyl)benzoyl]-2-(3,4-dichlorophenyl)morpholin-2-yl]ethyl 2-nitrobenzenesulfonate,
 (2R)-2-[4-{[3,5-bis(trifluoromethyl)phenyl]acetyl}-2-(3,4-dichlorophenyl)morpholin-2-yl]ethyl 4-chlorobenzenesulfonate,
 (2R)-2-[4-{[3,5-bis(trifluoromethyl)phenyl]acetyl}-2-(3,4-dichlorophenyl)morpholin-2-yl]ethyl 4-nitrobenzenesulfonate,
 (2R)-2-[4-{[3,5-bis(trifluoromethyl)phenyl]acetyl}-2-(3,4-dichlorophenyl)morpholin-2-yl]ethyl 2-nitrobenzenesulfonate,
 (+)-2-[3-(3,4-dichlorophenyl)-1-(3,4,5-trimethoxybenzoyl)piperidin-3-yl]ethyl 4-chlorobenzenesulfonate,
 (+)-2-[3-(3,4-dichlorophenyl)-1-(3,4,5-trimethoxybenzoyl)piperidin-3-yl]ethyl 4-nitrobenzenesulfonate,
 (+)-2-[3-(3,4-dichlorophenyl)-1-(3,4,5-trimethoxybenzoyl)piperidin-3-yl]ethyl 2-nitrobenzenesulfonate,
 (+)-2-[1-[3,5-bis(trifluoromethyl)benzoyl]-3-(3,4-dichlorophenyl)piperidin-3-yl]ethyl 4-chlorobenzenesulfonate,
 (+)-2-[1-[3,5-bis(trifluoromethyl)benzoyl]-3-(3,4-dichlorophenyl)piperidin-3-yl]ethyl 4-nitrobenzenesulfonate,
 (+)-2-[1-[3,5-bis(trifluoromethyl)benzoyl]-3-(3,4-dichlorophenyl)piperidin-3-yl]ethyl 2-nitrobenzenesulfonate,
 (+)-2-[1-{[3,5-bis(trifluoromethyl)phenyl]acetyl}-3-(3,4-dichlorophenyl)piperidin-3-yl]ethyl 4-chlorobenzenesulfonate,
 (+)-2-[1-{[3,5--bis(trifluoromethyl)phenyl]acetyl}-3-(3,4-dichlorophenyl)piperidin-3-yl]ethyl 4-nitrobenzenesulfonate, and
 (+)-2-[1-{[3,5-bis(trifluoromethyl)phenyl]acetyl}-3-(3,4-dichlorophenyl)piperidin-3-yl]ethyl 2-nitrobenzenesulfonate.

23. A compound according to claim 12, wherein said compound is selected from the group consisting of
 (2R)-2-[2-(3,4-dichlorophenyl)-4-(3,4,5-trimethoxybenzoyl)morpholin-2-yl]ethyl 4-chlorobenzenesulfonate,
 (2R)-2-[4-[3,5-bis(trifluoromethyl)benzoyl]-2-(3,4-dichlorophenyl)morpholin-2-yl]ethyl 4-chlorobenzenesulfonate,
 (2R)-2-[4-{[3,5-bis(trifluoromethyl)phenyl]acetyl}-2-(3,4-dichlorophenyl)morpholin-2-yl]ethyl 4-chlorobenzenesulfonate,
 (+)-2-[3-(3,4-dichlorophenyl)-1-(3,4,5-trimethoxybenzoyl)piperidin-3-yl]ethyl 4-chlorobenzenesulfonate,
 (+)-2-[3-[3,5-bis(trifluoromethyl)benzoyl]-1-(3,4-dichlorophenyl)piperidin-3-yl]ethyl 4-chlorobenzenesulfonate, and
 (+)-2-[1-{[3,5-bis(trifluoromethyl)phenyl]acetyl}-3-(3,4-dichlorophenyl)piperidin-3-yl]ethyl 4-chlorobenzenesulfonate.

24. A compound according to claim 1, wherein the compound is 2-[2-(3,4-dichlorophenyl)-4-(3,4,5-trimethoxybenzoyl)morpholin-2-yl]ethyl 4-chlorobenzenesulfonate.

25. A compound according to claim 1, wherein the compound is 2-[4-[3,5-bis(trifluoromethyl)benzoyl]-2-(3,4-dichlorophenyl)morpholin-2-yl]ethyl 4-chlorobenzenesulfonate.

26. A compound according to claim 12, wherein the compound is (2R)-2-[2-(3,4-dichlorophenyl)-4-(3,4,5-trimethoxybenzoyl)morpholin-2-yl]ethyl 4-chlorobenzenesulfonate.

27. A compound according to claim 12, wherein the compound is (2R) -2-[4-[3,5-bis(trifluoromethyl)benzoyl]-2-(3, 4-dichlorophenyl)morpholin-2-yl]ethyl 4-chlorobenzenesulfonate.

* * * * *